(12) United States Patent
Wollnik

(10) Patent No.: US 10,184,914 B2
(45) Date of Patent: Jan. 22, 2019

(54) PARALLEL PLATE-TYPE NON-UNIFORM ELECTRIC FIELD ION MOBILITY SPECTROMETRY DEVICE

(71) Applicant: SHIMADZU CORPORATION, Kyoto-shi, Kyoto (JP)

(72) Inventor: Hermann Wollnik, Fernwald (DE)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/556,878

(22) PCT Filed: Mar. 9, 2015

(86) PCT No.: PCT/JP2015/056814
§ 371 (c)(1),
(2) Date: Sep. 8, 2017

(87) PCT Pub. No.: WO2016/143030
PCT Pub. Date: Sep. 15, 2016

(65) Prior Publication Data
US 2018/0238831 A1    Aug. 23, 2018

(51) Int. Cl.
*G01N 27/62* (2006.01)
*H01J 49/06* (2006.01)
(52) U.S. Cl.
CPC ........ *G01N 27/624* (2013.01); *G01N 27/62* (2013.01); *H01J 49/063* (2013.01)
(58) Field of Classification Search
USPC ................................. 250/292, 286
See application file for complete search history.

(56) References Cited

U.S. PATENT DOCUMENTS 6,774,360 B2    8/2004  Guevremont et al.
7,550,717 B1    6/2009  Belford et al.
(Continued)

OTHER PUBLICATIONS

Communication dated Dec. 20, 2017, from the European Patent Office in counterpart European Application No. 15884526.3.
(Continued)

*Primary Examiner* — Kiet T Nguyen
(74) *Attorney, Agent, or Firm* — Sughrue Mion, PLLC

(57) ABSTRACT

In an ion separation space (15) between plate electrodes (11, 12), rod electrodes (16, 17) which are parallel to the plate electrodes as well as to each other are placed. An asymmetric pulse voltage is applied between the plate electrodes (11, 12), whereby high and low electric fields are alternately created within the ion separation space (15). A voltage obtained by adding an appropriate DC voltage to a voltage generated from the asymmetric pulse voltage by resistive division is applied to the rod electrodes (16, 17). At one point in time, since the outer edge of the rod electrodes (16, 17) has a predetermined potential, an electric field having curved equipotential surfaces bulging in the Y-axis direction is created within the space between those rod electrodes. Due to this electric field, ions carried by a buffer-gas flow move in zigzags, while experiencing a converging force in both X- and Y-axis directions. As a result, the ions having different mobility ratios are separated into laminar forms according to their mobility ratios and exit the ion separation space (15), forming a converged ion stream for each mobility ratio. Consequently, the ion transmission efficiency and separation performance are both improved.

10 Claims, 6 Drawing Sheets

(56) References Cited

U.S. PATENT DOCUMENTS

| | | | |
|---|---|---|---|
| 2009/0057546 A1* | 3/2009 | Giles | G01N 27/624 250/282 |
| 2012/0018631 A1* | 1/2012 | Giles | G01N 27/624 250/282 |
| 2015/0190815 A1* | 7/2015 | Hashimoto | G01N 27/624 204/645 |

OTHER PUBLICATIONS

Written Opinion dated Apr. 21, 2015 in application No. PCT/JP2015/056814.

International Preliminary Report on Patentability dated Sep. 12, 2017 PCT/JP2015/056814.

G. A. Eiceman et al., "Ion Mobility Spectrometry", CRC Press, 2013, pp. 127-131.

"1-8-4-1 Shitsuryou Bunseki Kanren Kiki/Haifuneeteddo Gijutsu/Ion Idoudo Sokutei/Ion Idoudo-kei (IMS), 1-8-4-1-2 High-Field Asymmetric Waveform Ion Mobility Spectrometry-Mass Spectrometry (FAIMS-MS) [1-8-4-1 Mass spectrometric Devices/Hyphenated Techniques/Ion Mobility Measurement/Ion Mobility Spectrometer (IMS), 1-8-4-1-2 High-Field Asymmetric Waveform Ion Mobility Spectrometry-Mass Spectrometry (FAIMS-MS)]", Japan Patent Office, [accessed on Jul. 1, 2014], the Internet <URL:http://www.jpo.go.jp/shiryou/s_sonota/hyoujun_gijutsu/mass/1-8-4.pdf>.

* cited by examiner

PARALLEL PLATE-TYPE NON-UNIFORM ELECTRIC FIELD ION MOBILITY SPECTROMETRY DEVICE

CROSS REFERENCE TO RELATED APPLICATIONS

This application is a National Stage of International Application No. PCT/JP2015/056814 filed Mar. 9, 2015, the contents of all of which are incorporated herein by reference in their entirety.

TECHNICAL FIELD

The present invention relates to an ion mobility spectrometer for separating ions by mobility, and more specifically, to a parallel-plate non-uniform electric field ion mobility spectrometer which uses parallel plate electrodes and separates ions by creating a temporal non-uniform electric field between those electrodes and making the ions move through this electric field.

BACKGROUND ART

When a molecular ion generated from a sample molecule is made to move through a gaseous (or liquid) medium by the effect of an electric field, the ion moves at a speed proportional to its mobility which is determined by the strength of the electric field, size of the molecule and other factors. Ion mobility spectrophotometry (IMS) is a measurement technique which utilizes this mobility for an analysis of sample molecules. Commonly known devices include a device in which ions separated according to their mobilities are introduced into and detected by a detector, as well as a device in which ions separated according to their mobilities are introduced into a mass analyzer or similar device to detect each ion after separating them according to their mass-to-charge ratios.

As one technique for the ion mobility spectrometry, a technique called the "differential mobility spectrometry" (DMS) has conventionally been known (see Patent Literature 1 and Non Patent Literature 1). Under a strong electric field, the mobility of an ion is no longer proportional to the strength of the electric field, and furthermore, the rate of change in the mobility is different for each ion species. DMS uses this principle to separate different ion species.

FIGS. 10 and 11 are schematic configuration diagrams of an ion separator section 1 in a conventional parallel plate electrode differential mobility spectrometer (DMS). FIGS. 10 and 11 illustrate the ion separator section 1 viewed from different directions.

In this ion separator section 1, the space sandwiched between upper and lower plate electrodes 11 and 12, both being parallel to the X-Z plane, serves as an ion separation space 15 for separating ions. From a pulse voltage generator 21, an asymmetric pulse voltage in which, as shown in FIG. 12, the period of time $T_H$ where the voltage value is at the high level (V1: the reverse polarity to the ions) is significantly different the period of time $T_L$ where the voltage value is at the low level (V2: the same polarity as the ions), is applied between the plate electrodes 11 and 12, which are held by spacers 13 and 14 at a predetermined distance from each other in the Y-axis direction. A flow of appropriate buffer gas, such as air, is formed at a constant flow velocity in the Z-axis direction within the ion separation space 15.

During the period of time $T_H$ where the applied voltage is at the high level, a high electric field having a relatively high field strength $E_H$ is formed within the ion separation space 15. During the period of time $T_L$ where the applied voltage is at the low level, a low electric field having a relatively low field strength $E_L$ is formed within the ion separation space 15. Now, consider the case where three kinds of ions with different mobilities are injected into the ion separation space 15 at a predetermined speed in the Z-axis direction, as shown in FIG. 10.

While the ions are moving forward, the strength of the electric field within the ion separation space 15 alternates between $E_H$ and $E_L$. Consequently, the ions travelling through the ion separation space 15 alternately experience a force due to the high electric field with field strength $E_H$ and a force due to the low electric field with field strength $E_L$. For the ions travelling through the ion separation space 15, this situation can be regarded as the presence of a high electric field region 100 with field strength $E_H$ and a low electric field region 101 with field strength $E_L$ alternately arranged along the Z axis, as shown in FIG. 10. The ratio of the length of the high electric field region 100 to that of the low electric field region 101 in the Z-axis direction is determined by the ratio of the high-level-voltage period $T_H$ to the low-level-voltage period $T_L$.

When the ions pass through the high electric field region 100, the three kinds of ions all move closer to the upper plate electrode 11 due to the force from this electric field. In this phase, the three ions, whose mobilities within the high electric field region 100 are $\mu_{H1}$, $\mu_{H2}$ and $\mu_{H3}$, have speeds of $E_H \cdot \mu_{H1}$, $E_H \cdot \mu_{H2}$ and $E_H \cdot \mu_{H3}$, respectively. By comparison, when the ions pass through the low electric field region 101, the three kinds of ions all move closer to the lower plate electrode 12 due to the force from this electric field. In this phase, the three ions, whose mobilities within the low electric field region 101 are $\mu_{L1}$, $\mu_{L2}$ and $\mu_{L3}$, have speeds of $E_L \cdot \mu_{L1}$, $E_L \cdot \mu_{L2}$ and $E_L \cdot \mu_{L3}$, respectively. Consequently, each of the three ions moves in zigzags within the ion separation space 15.

For one kind of ion for which the ratio of the mobility within the high electric field region 100 to the mobility within the low electric field region 101 is $\alpha_1 = \mu_{H1}/\mu_{L1}$ (which is hereinafter simply called the "mobility ratio"), if the separation condition is determined so as to satisfy $T_H \cdot E_H \cdot \mu_{H1} = T_L \cdot E_L \cdot \mu_{L1}$, the amount of movement of this ion species in the Y-axis direction within the high electric field region 100 equals that of the movement in the Y-axis direction (in the negative direction) within the low electric field region 101. Therefore, this ion species moves in zigzags along the central axis C while being carried by the buffer-gas flow, to eventually reach the exit end of the ion separation space 15. The path of this ion species is schematically indicated by line "a" in FIG. 10.

For the other two ion species whose mobility ratios are different from $\alpha_1$, i.e. $\alpha_2 = \mu_{H2}/\mu_{L2}$ and $\alpha_3 = \mu_{H3}/\mu_{L3}$, the amount of movement in the Y-axis direction within the high electric field region 100 is not equal to that of the movement in the Y-axis direction within the low electric field region 101. Therefore, as they move forward within the ion separation space 15, those ions gradually deviate from the central axis C (see trajectories "b" and "c" in FIG. 10). Upon reaching a sufficiently large distance from the central axis C, the ions come in contact with the plate electrode 11 or 12 and disappear. Thus, the DMS can isolate and extract only an ion species having a specific mobility ratio.

In the previously described parallel-plate electrode DMS, the ions passing through the ion separation space 15 experience the force due to the electric field only in the Y-axis direction (positive or negative). Accordingly, if an ion having the mobility ratio of $\alpha_1$ is incident on a point displaced from the central axis C on the entrance end plane (which is an end plane parallel to the X-Y plane) of the ion separation space 15, this ion will exit from the ion separation space 15 at a point displaced from the central axis C on the exit end plane of the same space. This means that, if a group of ions having the same mobility ratio are spatially spread when they are introduced into the ion separation space 15, those ions will remain spatially spread even when they exit from the ion separation space 15. Furthermore, even a group of ions having the same mobility ratio and incident on the same point on the entrance end plane of the ion separation space 15 do not always follow the path "a" along the central axis C, since they vary in the amount of initial energy, incident angle and other relevant quantities. Therefore, ions having one mobility ratio are typically spread over a wide area, e.g. as indicated by "A" in FIG. 11, when they arrive at the exit end plane of the ion separation space 15.

Such a spatial spread of the ions having the same mobility ratio lowers the transmission efficiency of the ions when the ions arriving at a specific position are to be extracted through an aperture plate, skimmer or similar device placed outside the exit end of the ion separation space 15. Consequently, it will be difficult to improve the measurement sensitivity. Furthermore, when a plurality of ion species having different mobility ratios are to be separated from each other and individually extracted, it is likely that other ion species will be mixed with the intended one and consequently lower the measurement accuracy.

As an improved version of the DMS, a device using cylindrical electrodes as shown in FIG. 13 has also been commonly known (see Non Patent Literature 2). In this DMS, as in the aforementioned example, an asymmetric pulse voltage is applied between the concentrically arranged cylindrical electrodes 110 and 120, creating an electric field similar to the previously described one within the ion separation space 15 between those cylindrical electrodes 110 and 120. However, in this device, the equipotential surfaces due to the electric field created between the pair of cylindrical electrodes 110 and 120 have a smaller radius of curvature at a closer position to the inner side, or to the cylindrical electrode 120. Therefore, a force which reduces the spatial spread of the ions travelling through the ion separation space 15 acts on those ions, making them converge on an arc-shaped specific center line B.

However, even such a DMS cannot produce a significant ion-converging effect in the lateral direction of the ion stream, and therefore, is not sufficiently effective for improving the ion transmission efficiency. Furthermore, producing the cylindrical electrodes with a high level of mechanical precision incurs a considerably high amount of cost as compared to the parallel-plate electrodes. Accordingly, a configuration as shown in FIG. 13 is unfavorable in terms of the device cost.

CITATION LIST

Patent Literature

Patent Literature 1: U.S. Pat. No. 6,774,360 B

Non Patent Literature

Non Patent Literature 1: "1-8-4-1 Shitsuryou Bunseki Kanren Kiki/Haifuneeteddo Gijutsu/Ion Idoudo Sokutei/Ion Idoudo-kei (IMS), 1-8-4-1-2 High-Field Asymmetric Waveform Ion Mobility Spectrometry-Mass Spectrometry (FAIMS-MS) [1-8-4-1 Mass spectrometric Devices/Hyphenated Techniques/Ion Mobility Measurement/Ion Mobility Spectrometer (IMS), 1-8-4-1-2 High-Field Asymmetric Waveform Ion Mobility Spectrometry-Mass Spectrometry (FAIMS-MS)]", Japan Patent Office, [accessed on Jul. 1, 2014], the Internet Non Patent Literature 2: G. A. Eiceman and two other authors, "Ion Mobility Spectrometry", CRC Press, 2013

SUMMARY OF INVENTION

Technical Problem

The present invention has been developed to solve the previously described problem. Its primary objective is to provide a parallel-plate non-uniform electric field ion mobility spectrometer which uses parallel-plate electrodes for creating a non-uniform electric field and yet is capable of achieving a high level of ion transmission efficiency as well as a high level of ion separation performance.

Solution to Problem

The present invention developed for solving the previously described problem is a parallel-plate non-uniform electric field ion mobility spectrometer including a pair of parallel plate electrodes and a main voltage generator for applying an asymmetric pulse voltage to the plate electrodes so as to create a non-uniform electric field within an ion separation space between the plate electrodes, for separating ions according to mobility by introducing ions derived from a sample component into the ion separation space while a flow of buffer gas is passed through the ion separation space at a constant flow velocity in the same direction as the direction in which the ions are introduced, and by controlling the movement of the ions by an effect of the non-uniform electric field while the ions are carried by the flow of buffer gas, the ion mobility spectrometer including:

a) at least two electric-field correction electrodes located within the ion separation space sandwiched between the plate electrodes, the electric-field correction electrodes shaped like rods extending in the same direction as the passing direction of the ions and facing each other across an area where the ions pass through; and b) an electric-field correction voltage generator for applying, to the electric-field correction electrodes, a voltage obtained by adding a predetermined DC voltage and a pulse voltage synchronized with the asymmetric pulse voltage.

The "asymmetric pulse voltage" is a pulse voltage in which the period of time where the voltage value is at the high level is not equal to the period of time where the voltage value is at the low level, i.e. a pulse voltage whose duty cycle is not 0.5 (50%).

In the ion mobility spectrophotometer according to the present invention, the electric field created within the ion separation space sandwiched between the pair of plate electrodes during the period of time where the high-level voltage in the asymmetric pulse voltage is applied between those plate electrodes is different from the electric field created during the period of time where the low-level voltage is applied. If the electric-field correction electrodes are not present within the ion separation space, the equipotential surfaces in the electric field created within the ion separation space become substantially parallel to the plate electrodes. Ions moving through this electric field experience a force in a direction substantially orthogonal to those equipotential surfaces. Therefore, no ion-converging force acts on the ions if the equipotential surfaces are substantially parallel to the plate electrodes as just mentioned.

By comparison, in the ion mobility spectrometer according to the present invention, the potential at the (spatial) position where an electric-field correction electrode is placed within the ion separation space is determined by the voltage applied from the electric-field correction voltage generator to the electric-field correction electrode concerned. The spacing and shape of the equipotential surfaces in the electric field created within the space between the electric-field correction electrode and each of the plate electrodes facing each other across that correction electrode are dependent on the shape and size of the electric-field correction electrode, or on its position and the applied voltage. Therefore, by appropriately determining the shape, size and other parameters concerning the electric-field correction electrodes as well as appropriately setting the applied voltage, the equipotential surfaces in the electric field created within the space sandwiched between the electric-field correction electrodes in the ion separation space are deformed into curved surfaces, causing an ion-converging force to act on ions which move within the electric field. While being affected by this force, each ion moves in zigzags according to its mobility ratio due to the effect of the asymmetric pulse voltage. As a result, an ion stream which is converged to a certain degree is obtained for each mobility ratio at the exit end of the ion separation space. Therefore, for example, by placing a skimmer or similar device at the position where the ion stream showing the mobility ratio of interest arrives, that ion of interest can be extracted with high efficiency.

In the parallel-plate non-uniform electric field ion mobility spectrometer according to the present invention, the electric-field correction voltage generator needs to apply, to the electric-field correction electrodes, a pulse voltage which is synchronized with the asymmetric pulse voltage applied to the plate electrodes and whose DC voltage level is appropriately adjusted.

Accordingly, in the parallel-plate non-uniform electric field ion mobility spectrometer according to the present invention, the electric-field correction voltage generator may preferably be configured to add the predetermined DC voltage and a pulse voltage generated from the asymmetric pulse voltage by resistive division.

This configuration allows the amplitude of the pulse voltage applied to the electric-field correction electrodes to be determined by merely adjusting the resistance values for the resistive division.

In the parallel-plate non-uniform electric field ion mobility spectrometer according to the present invention, there is no specific limitation on the cross-sectional outer-edge shape of the electric-field correction electrodes. For example, the cross-sectional outer-edge shape may be selected from circular, elliptical, polygonal, square and rectangular shapes. The cross-sectional outer-edge does not need to be entirely the aforementioned shape; the minimum requirement is that the cross-sectional outer-edge shape should have a circular shape, elliptical shape or any one of the aforementioned shapes at least on the side facing the central axis, i.e. on the side facing the space where ions pass through.

Under typical conditions, the length of the electric-field correction electrodes only needs to be roughly equal to the length of the pair of plate electrodes in the ion-passage direction. However, the electric-field correction electrodes may additionally have an extended portion extending beyond the ion exit end of the plate electrodes. The electric-field correction electrodes arranged within the ion separation space normally extend in the same direction as the flow of the ion-carrying buffer gas. This makes the electric-field correction electrodes double as a guide for helping the buffer gas to flow straight. Accordingly, providing the electric-field correction electrodes with the extended portion in the aforementioned manner produces the effect of suppressing turbulence of the flow of the buffer gas in the area outside the ion exit end of the plate electrodes, thereby preventing the ions separated by mobility ratio from being mixed with each other.

In the parallel-plate non-uniform ion mobility spectrometer according to the present invention, the main voltage generator may be configured to apply, to one of the pair of plate electrodes, an additional DC voltage higher than the potential of the other plate electrode, and the electric-field correction voltage generator may be configured to apply, to one of a pair of the electric-field correction electrodes facing each other across an ion stream, an additional DC voltage higher than the potential of the other electric-field correction electrode.

The amount of each of these additional DC voltages is much smaller than the entire voltage applied the electrode concerned. The application of such additional DC voltages causes a slight imbalance of the electric field, making it possible to slightly shift the positions at which the ion streams which are separately guided according to their mobility ratios arrive.

As a first mode of the present invention, the parallel-plate non-uniform electric field ion mobility spectrometer may include a single detector having a size that allows selective detection of only one ion stream having a specific mobility ratio among a plurality of ion streams formed by the ions separated by mobility ratio as a result of passing through the ion separation space, the single detector placed at a position at which the ion stream concerned arrives.

The parallel-plate non-uniform electric field ion mobility spectrometer according to this first mode can selectively detect ions having a specific mobility ratio.

As a second mode of the present invention, the parallel-plate non-uniform electric field ion mobility spectrometer may include two or more detectors having sizes that allow respective and selective detection of two or more ion streams among a plurality of ion streams formed by the ions separated by mobility ratio as a result of passing through the ion separation space, the two or more detectors placed at positions at which the two or more ion streams respectively arrive.

The parallel-plate non-uniform electric field ion mobility spectrometer according to this second mode can simultaneously detect two or more kinds of ions having specific mobility ratios which differ from each other.

As a third mode of the present invention, the parallel-plate non-uniform electric field ion mobility spectrometer may include a single position-sensitive detector placed at positions at which two or more ion streams having specific mobility ratios which differ from each other arrive among a plurality of ion streams formed by the ions separated by mobility ratio as a result of passing through the ion separation space, so as to separately detect each of the two or more ion streams with the position-sensitive detector.

One example of the position-sensitive detector is a two-dimensional detector having a large number of micro-sized detection elements arrayed in a two-dimensional form. The parallel-plate non-uniform electric field ion mobility spectrometer according to this third mode can also simultaneously detect two or more kinds of ions having specific mobility ratios which differ from each other.

The parallel-plate non-uniform electric field ion mobility spectrometer according to the present invention minimally requires only two electric-field correction electrodes. It is also possible to arrange three or more electric-field correction electrodes substantially parallel to each other and allow an ion stream to pass through each of the spaces formed between the neighboring electric-field correction electrodes, whereby, for example, a greater amount of ions can be separated according to their mobilities.

That is to say, the parallel-plate non-uniform electric field ion mobility spectrometer according to the present invention may include three or more of the electric-field correction electrodes arranged parallel to each other within the space between the pair of plate electrodes and spaced in the planer direction of the plate electrodes so that each space formed between the neighboring electric-field correction electrodes serves as the ion separation space.

In the parallel-plate non-uniform electric field ion mobility spectrometer according to the present invention, two or more groups of the electric-field correction electrodes separated from each other in the direction orthogonal to the plate electrodes may be provided, each group including a plurality of electrodes facing each other across an area where ions pass through, and the electric-field correction voltage generator may be configured to be capable of applying a different voltage for each of the two or more groups of the electric-field correction electrodes.

This configuration makes it possible to finely tune the electric field distribution within the space between the pair of plate electrodes in the direction orthogonal to the plate electrodes, so as to more properly separate ions.

The various previously described configurations applied in the case of using a pair of (two) electric-field correction electrodes can also be similarly adopted in the case of using three or more electric-field correction electrodes.

Advantageous Effects of the Invention

In the parallel-plate non-uniform electric field ion mobility spectrometer according to the present invention, ions which have been separated according to their mobility ratios can be spatially converged and extracted from the ion separation space by means of a combination of simple-shaped electrodes, such as parallel plate electrodes and rod electrodes. Consequently, a greater amount of ions are supplied for such operations as the detection of ions having a specific mobility ratio or the introduction of ions into a device in the next stage (e.g. mass spectrometer unit), so that the detection sensitivity or measurement sensitivity will be improved.

Additionally, the parallel-plate non-uniform electric field ion mobility spectrometer according to the present invention provides an improved capability to separate ions according to their mobility ratios, which reduces the mixture of ions having different mobility ratios and consequently improves the detection sensitivity or measurement sensitivity. The present invention is also advantageous in terms of the device cost since the device structure will not become complex.

DESCRIPTION OF EMBODIMENTS

An ion mobility spectrometer as one embodiment of the present invention is hereinafter described with reference to the attached drawings.

Figure 1:
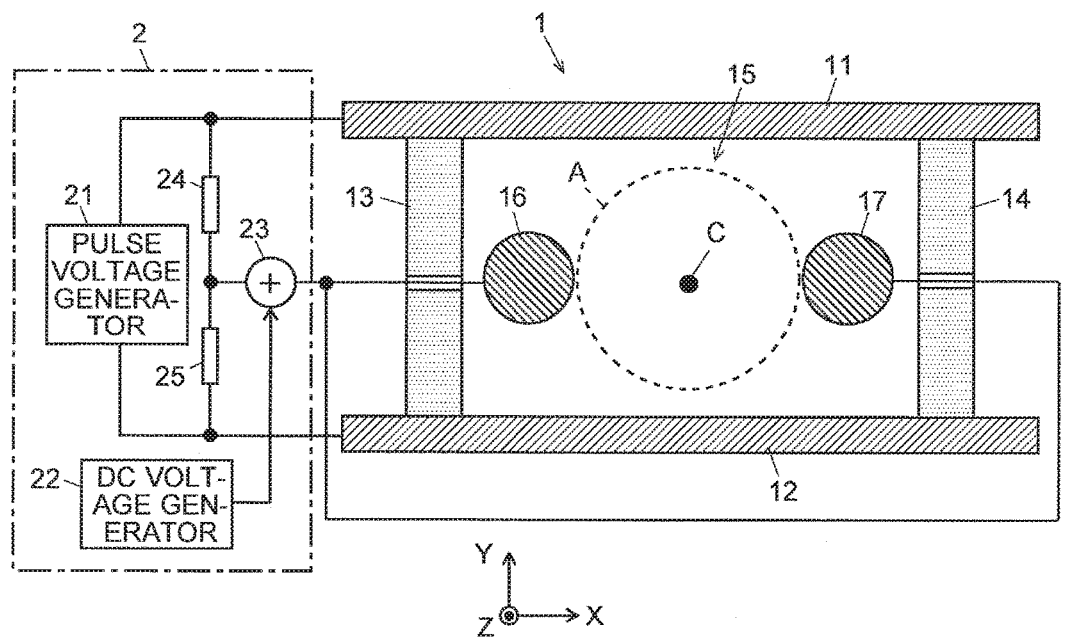
FIG. 1 is a schematic configuration diagram of an ion separator section in an ion mobility spectrometer as one embodiment of the present invention.
Figure 2:
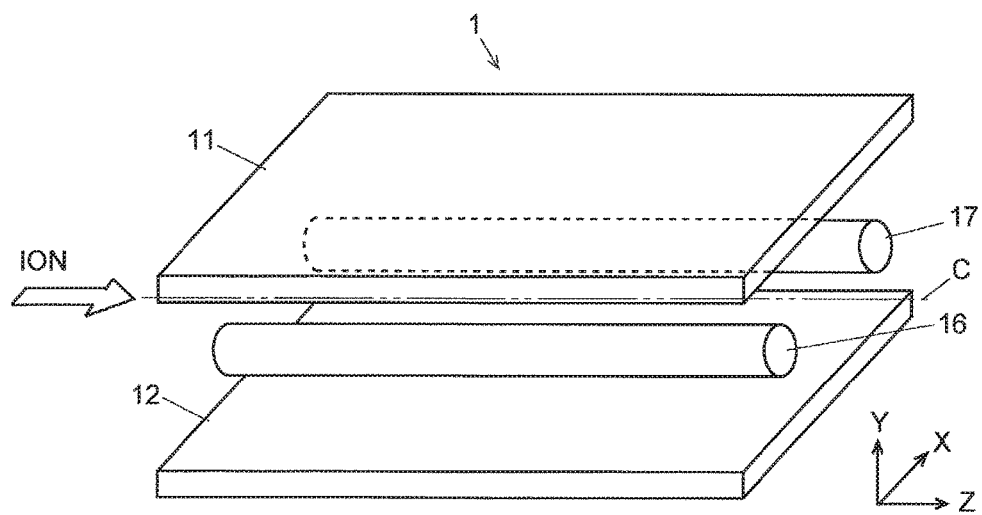
FIG. 2 is a schematic perspective view of the ion separator section in the ion mobility spectrometer of the present embodiment.

FIG. 1 is a schematic configuration diagram of an ion separator section in the ion mobility spectrometer of the present embodiment. FIG. 2 is a schematic perspective view of the ion separator section in the ion mobility spectrometer of the same embodiment.

Components which are identical or correspond to those used in the conventional ion mobility spectrometer described using FIGS. 10-13 are denoted by the same numerals.

Similarly to the conventional device, the ion mobility spectrometer in the present embodiment has a pair of plate electrodes 11 and 12 held by spacers 13 and 14 at a predetermined distance from each other in the Y-axis direction, with an ion separation space 15 formed in between. Within this ion separation space 15, two rod electrodes 16 and 17 are arranged at a certain distance from each other in the X-axis direction, with the central axis C in between. These rod electrodes 16 are 17 consist of cylindrical conductors extending in the Z-axis direction. The two rod electrodes 16 and 17 are parallel to each other as well as to the plate electrodes 11 and 12.

Figure 12:
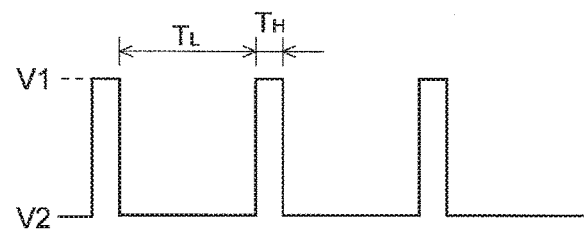
FIG. 12 is a waveform diagram showing one example of the asymmetric pulse voltage applied to the plate electrodes in the conventional DMS.
Figure 13:
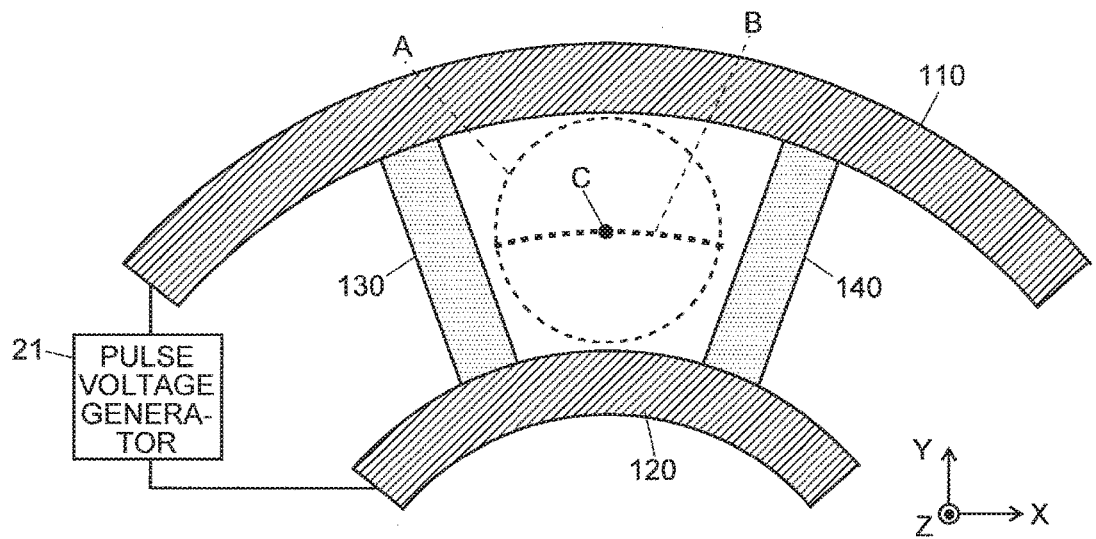
FIG. 13 is a schematic configuration diagram of the ion separator section in another conventional DMS.

The voltage generator 2 includes a pulse voltage generator 21 acting as the main voltage generator, which is also provided in the conventional device, as well as two resistors 24 and 25, a DC voltage generator 22 and a voltage adder 23, which constitute the electric-field correction voltage generator for applying a voltage to the rod electrode 16 and 17. The pulse voltage generator 21 applies an asymmetric pulse voltage between the upper and lower plate electrodes 11 and 12. This voltage is similar to the one used in the conventional device, as shown in FIG. 12.

A pulse voltage generated by dividing this asymmetric pulse voltage by the serially connected resistors 24 and 25, and the DC voltage with a predetermined voltage value V0 generated by the DC voltage generator 22, are added by the voltage adder 23 and commonly applied to the two rod electrodes 16 and 17. The voltage thus applied can also be regarded as a voltage generated by reducing the amplitude (or pulse height, V1-V2) of the asymmetric pulse voltage according to the resistance ratio of the resistors 24 and 25, with its DC voltage level appropriately shifted (i.e. with an offset voltage given) by the predetermined voltage value V0. Needless to say, the rise and fall of the pulse voltage applied to the rod electrodes 16 and 17 is synchronized with those of the asymmetric pulse voltage; the voltage value applied to the rod electrodes 16 and 17 alternately changes with the switching of the phase between the period of time $T_H$ where the asymmetric pulse voltage is at the high level (V1) and the period of time $T_L$ where the asymmetric pulse voltage is at low high level (V2).

Figure 11:
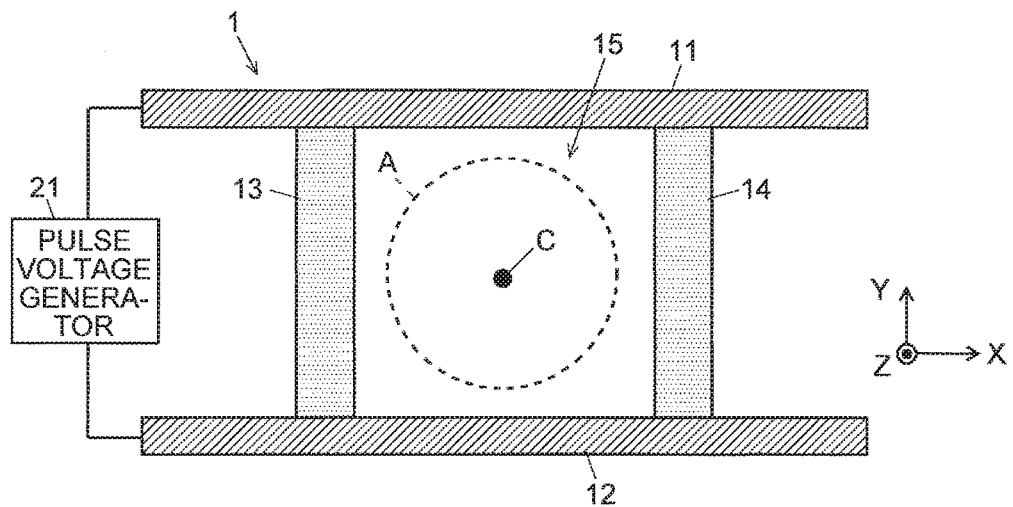
FIG. 11 is a schematic configuration diagram of the ion separator section in the conventional DMS.

If there is no rod electrodes 16 and 17 within the ion separation space 15, i.e. in the case of the configuration as shown in FIG. 11, the equipotential surfaces in the electric field created within the ion separation space 15 at one point in time are substantially parallel to the plate electrodes 11 and 12. By comparison, in the ion mobility spectrometer of the present embodiment, the potential on the outer cylindrical surface of each of the rod electrodes 16 and 17 at one point in time becomes a predetermined potential corresponding to the voltage applied to the plate electrodes 11 and 12 at that point in time. Therefore, this potential on the rod electrodes 16 and 17 determines the shape, density (i.e. potential gradient) and other characteristics of the equipotential surfaces in the space between the upper plate electrode 11 and the rod electrodes 16 and 17, those of the equipotential surfaces in the space between the lower plate electrode 12 and the rod electrodes 16 and 17, as well as those of the equipotential surfaces in the space between the two rod electrodes 16 and 17.

Figure 3:
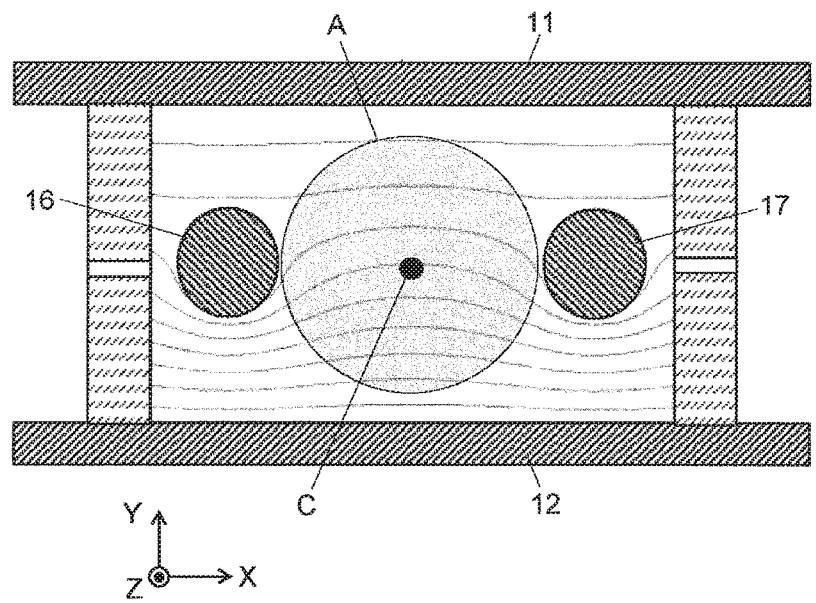
FIG. 3 is a diagram showing the result of a simulation of the equipotential surfaces formed by an electric field created within the ion separation space in the ion mobility spectrometer of the present embodiment.

FIG. 3 shows one example of the result of a simulation of the equipotential surfaces formed by an electric field created within the ion separation space 15 at one point in time where the high-level voltage value V1 is applied between the plate electrodes 11 and 12 (actually, those surfaces are drawn by translating equipotential lines on the X-Y plane along the Z-axis). As noted earlier, the outer circumferential surfaces of the rod electrodes 16 and 17 have a predetermined equal potential. Therefore, the equipotential surfaces in the present example are densely formed in the space between the lower plate electrode 12 and the rod electrodes 16 and 17. In the vicinity of the rod electrodes 16 and 17, those equipotential surfaces are curved along the outer circumferential surfaces of the rod electrodes 16 and 17. As a result, the equipotential surfaces in the space between the rod electrodes 16 and 17 become curved surfaces bulging upward, as shown in FIG. 3. This shape is analogous to that of the equipotential surfaces formed in the ion separator section which uses the cylindrical electrodes shown in FIG. 13. Needless to say, the shape of the equipotential surfaces changes depending on whether the phase of the asymmetric pulse voltage is within the period of time $T_H$ where the voltage is at the high level or within the period of time $T_L$ where the voltage is at the low level.

A force which acts on ions moving in an electric field due to the effect of the same field is substantially orthogonal to the equipotential surfaces. If the equipotential surfaces in the electric field created within the ion separation space 15 are substantially parallel to the plate electrodes 11 and 12, the ions merely experience a vertical-swinging force (in the Y-axis direction in FIGS. 1-3) every time the electric field is switched between the high and low levels according to the applied asymmetric pulse voltage; there is no force causing the ions to converge onto a specific position or region. Therefore, the spatial spread of the ions observed at their incidence into the ion separation space 15 does not decrease even after they pass through the ion separation space 15. On the contrary, ions which have the same mobility ratio and yet are varied in energy and/or incident angle will have their trajectories spread while they pass through the ion separation space 15.

By comparison, in the case where the equipotential surfaces in the space surrounded by the plate electrodes 11 and 12 as well as the rod electrodes 16 and 17 are shaped like curved surfaces as shown in FIG. 3, ions located in the vicinity of the rod electrodes 16 and 17 experience a force which causes the ions to move closer to the Y-Z plane passing through the central axis C. This force increases with a decrease in the distance to the rod electrode 16 or 17. Similarly, in the case where an electric field which is different from the one shown in FIG. 3 (i.e. which corresponds to the low electric field region) is formed within the ion separation space 15, ions located in the vicinity of the rod electrodes 16 and 17 experience a force which causes the ions to come closer to the Y-Z plane passing through the central axis C, although the positive/negative direction for the movement of the ions in the Y-axis direction is reversed. Thus, the spread of the ions carried by the flow of the buffer gas through the ion separation space 15 is reduced in both width (X-axis) and height (Y-axis) directions, and the ions converge into the vicinity of the Y-Z plane passing through the central axis C while being gradually separated according to their mobility ratios.

Figure 4:
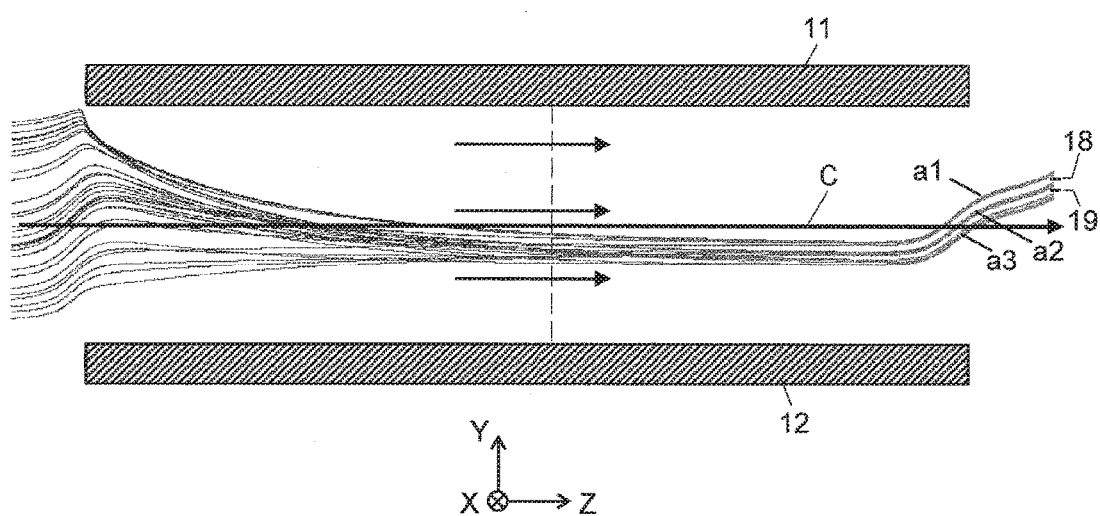
FIG. 4 is a diagram showing the result of a simulation of the ion trajectories within the ion separation space in the ion mobility spectrometer of the present embodiment.

FIG. 4 is a diagram showing the result of a simulation of the ion trajectories in the ion separation space 15. The conditions of this trajectory simulation were set so as to simulate three kinds of ions having different mobility ratios incident on the almost entire area of the ion separation space 15 between the plate electrodes 11 and 12. The voltages applied to the plate electrodes 11 and 12 as well as the rod electrodes 16 and 17 were set so that an almost highest ion-separation performance would be achieved. As can be seen in FIG. 4, while being carried through the ion separation space 15 by the buffer-gas flow, the three kinds of ions having different mobility ratios gradually converge into a central region, being separated into laminar forms in the Y-axis direction. Eventually, the ions are separated into streams following different paths "a1", "a2" and "a3" according to the ion species, and exit the ion separation space 15. Through not evident in FIG. 4, each ion stream is also sufficiently converged in the X-axis direction.

In the example shown in FIG. 4, two extremely thin electrode plates 18 and 19 are arranged outside the exit end plane of the ion separation space 15 so as to separate the three layers of the ion paths. A predetermined voltage having the same polarity as the ions is applied to these electrode plates 18 and 19. Due to this voltage, the ion stream following the path a1 passing through the space above the electrode plate 18 is slightly deflected upward, while the ion stream following the path a3 passing through the space below the electrode plate 19 is slightly deflected downward.

Thus, the three ion streams following the paths a1, a2 and a3 are further separated from each other. This facilitates the detection or collection of each kind of ions separated by mobility ratio.

Figure 7:
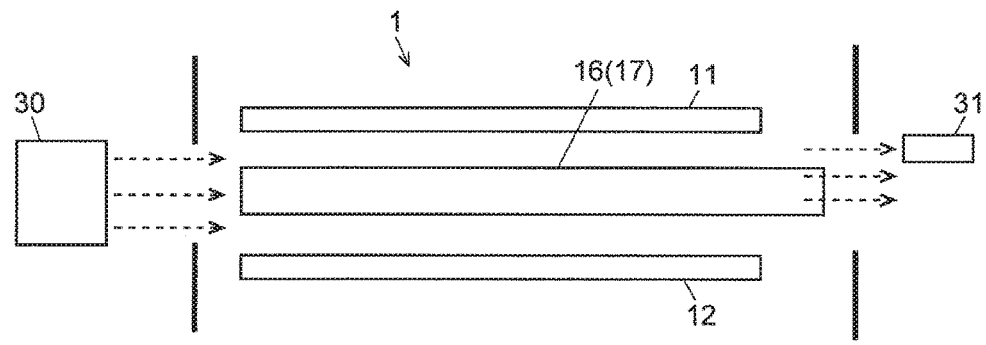
FIG. 7 is a schematic configuration diagram of one mode of the ion mobility spectrometer according to the present invention.
Figure 8:
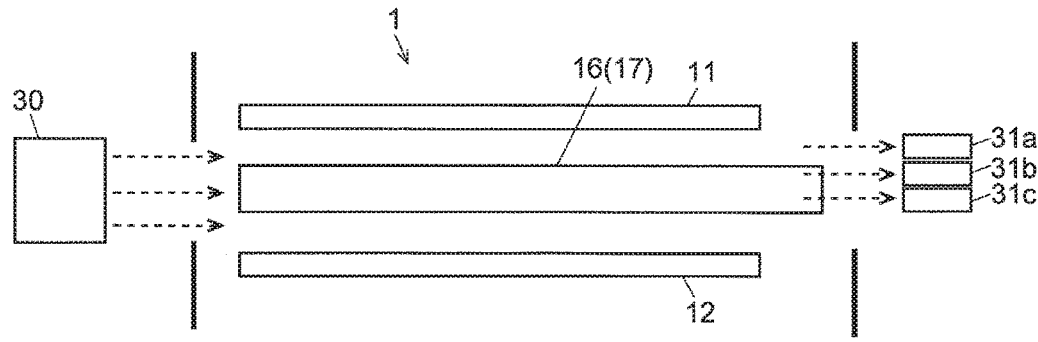
FIG. 8 is a schematic configuration diagram of another mode of the ion mobility spectrometer according to the present invention.
Figure 9:
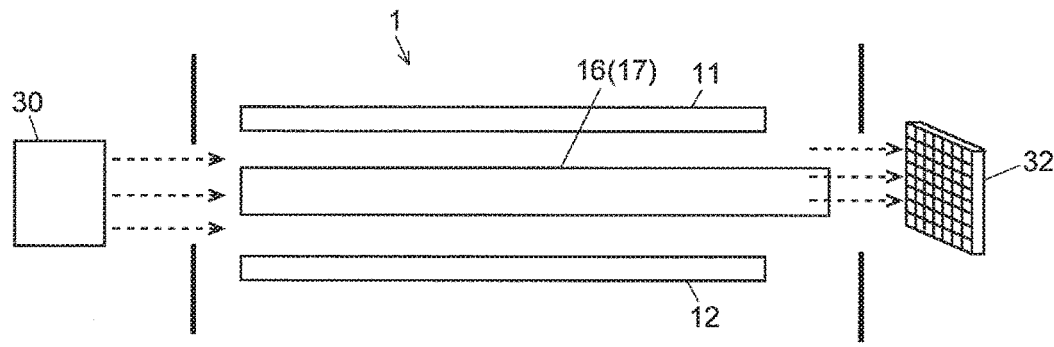
FIG. 9 is a schematic configuration diagram of another mode of the ion mobility spectrometer according to the present invention.
Figure 10:
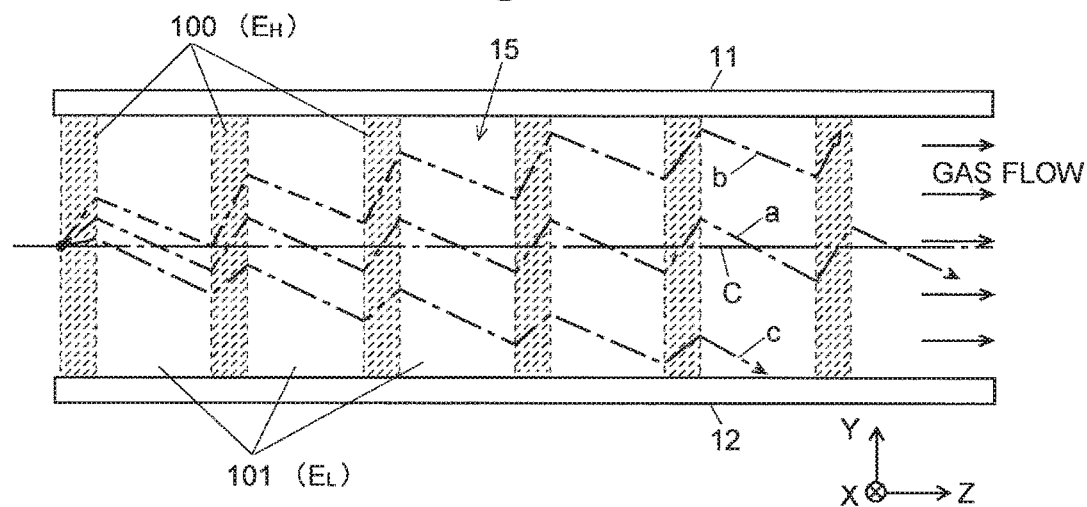
FIG. 10 is a diagram illustrating the principle of the ion separation in a conventional DMS.

FIGS. 7-9 are schematic configuration diagrams showing some modes of the ion mobility spectrometer using the ion separator section 1 configured in the previously described manner.

In a mode of the ion mobility spectrometer shown in FIG. 7, ions (or electrically charged aerosol or the like) produced in an ion source 30 are introduced into the ion separation space 15 of the ion separator section 1, where the ions having different mobility ratios are separated into laminar forms, as described earlier. A detector 31 which has an extremely small detection surface, or which collects and detects only ions arriving at an extremely small area, is placed at a predetermined position outside the exit end plane of the ion separation space 15. This detector 31 receives only an ion stream forming one separate laminar flow which contains ions having one specific mobility ratio; ion streams which contain ions having other mobility ratios do not enter the detector 31. Thus, the present ion mobility spectrometer can selectively detect ions having a specific mobility ratio.

The mobility ratio of the ions to be detected can be changed by controlling the value of the DC voltage generated from the DC voltage generator 22 so as to change the positions at which the ion streams separated into the laminar forms arrive, or by mechanically changing the placement position of the detector 31.

In the ion mobility spectrometer shown in FIG. 7, the rear-edge ends of the rod electrodes 16 and 17 extend beyond those of the plate electrodes 11 and 12. Since the rod electrodes 16 and 17 extend in the same direction as the flow direction of the buffer gas (Z-axis direction) within the ion separation space 15, the rear-edge end portions of the rod electrodes 16 and 17 protruding from the exit end plane of the ion separation space 15 in the aforementioned manner have the effect of reducing the turbulence of the buffer gas flowing out of the exit end plane of the ion separation space 15, i.e. they straighten the buffer-gas flow. This prevents the ion streams separated into laminar forms according to their mobility ratios from being mixed with each other due to turbulence of the buffer-gas flow immediately after leaving the exit end plane of the ion separation space 15.

In a mode of the ion mobility spectrometer shown in FIG. 8, a plurality of detectors 31a, 31b and 31c (in the present example, three detectors) each of which has an extremely small detection surface, or each of which collects and detects only ions arriving at an extremely small area, are arranged in the Y-axis direction at a predetermined position outside the exit end plane of the ion separation space 15. Each of the detectors 31a, 31b and 31c receives only an ion stream forming one separate laminar flow which contains ions having one specific mobility ratio. Accordingly, the present ion mobility spectrometer can concurrently detect three kinds of ions having specific mobility ratios which differ from each other. The present ion mobility spectrometer may also be configured so that the position of each of the plurality of detectors 31a, 31b and 31c can be independently changed, or so that the plurality of detectors 31a, 31b and 31c are combined as one integrated unit whose position can be changed.

In a mode of the ion mobility spectrometer shown in FIG. 9, a two-dimensional detector 32 as the position-sensitive detector is provided outside the exit end plane of the ion separation space 15. One example of the two-dimensional detector 32 is the combination of a microchannel plate (MCP) for converting ions into electrons, a fluorescent screen for converting electrons into photons, and a two-dimensional image sensor including a large number of micro-sized photodetector elements for converting light into electric signals. In this ion mobility spectrometer, the positions at which the ion streams separated into laminar forms according to their mobility ratios have arrived can be obtained as the address information on the two-dimensional detector 32. Therefore, signal intensities which respectively correspond to a plurality of ion streams can be individually obtained.

In the ion mobility spectrometers shown in FIGS. 7-9, a detector is used to detect ions separated according to their mobility ratios in the ion separator section 1. In place of the detector, an ion introduction element, such as a skimmer or aperture plate, may be provided to extract an ion stream containing ions having one or more predetermined mobility ratios through the ion introduction element, and introduce the extracted ions into a mass analyzer, such as a quadrupole mass filter. With this system, ions which have been separated according to their mobility ratios can be further separated according to their mass-to-charge ratios and detected.

Figure 6:
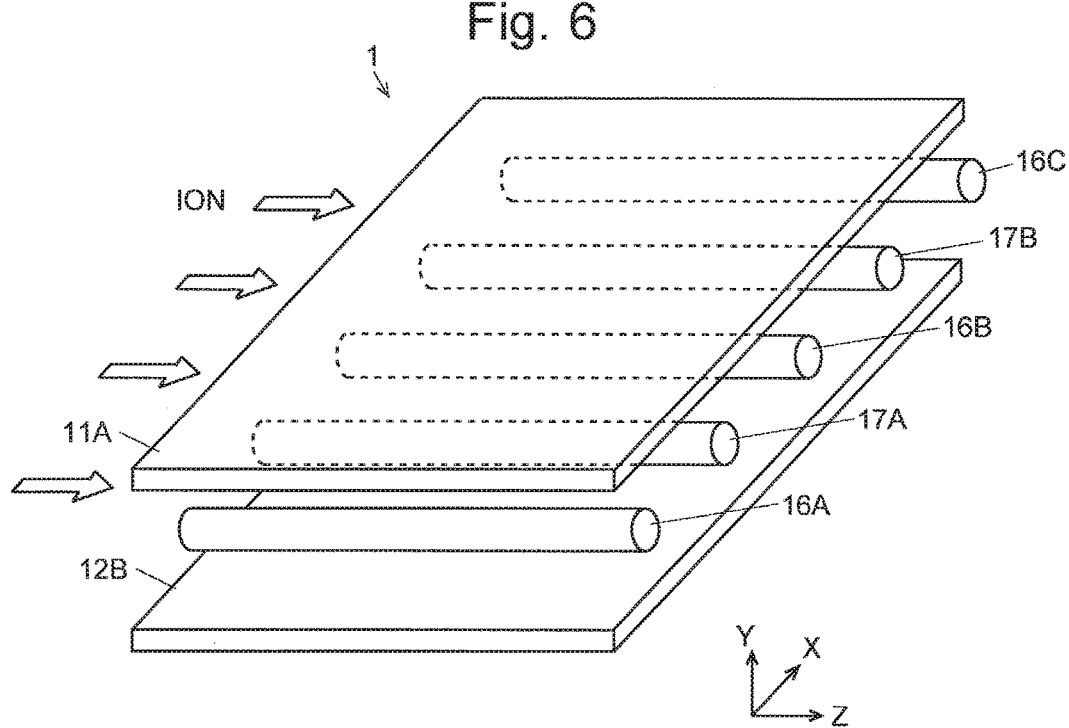
FIG. 6 is a schematic perspective view of an ion separator section in an ion mobility spectrometer as still another embodiment of the present invention.

The ion mobility spectrometers in the previous embodiment are provided with only two rod electrodes 16 and 17 within the space between the pair of plate electrodes 11 and 12, with a stream of buffer gas passed through the space between the two rod electrodes 16 and 17 to carry the ions. It is also possible to provide a greater number of rod electrodes parallel to each other and utilize all spaces formed between the neighboring rod electrodes. FIG. 6 shows a schematic perspective view of the ion separator section 1 in an ion mobility spectrometer according to another embodiment of the present invention in which such a structure is adopted. In this example, five rod electrodes 16A, 17A, 16B, 17B and 16C are arranged within the space between a pair of plate electrodes 11A and 12A which are considerably wide in the X-axis direction. The four spaces formed between the neighboring rod electrodes are used for the conveyance and separation of the ions. Since the same voltage is commonly applied to the five rod electrodes 16A, 17A, 16B, 17B and 16C, the same ion-separating condition is created in any of those four spaces, so that ion streams separated into laminar forms according to their mobility ratios are obtained within each of those spaces. Thus, a large amount of ions can be concurrently separated.

Figure 5:
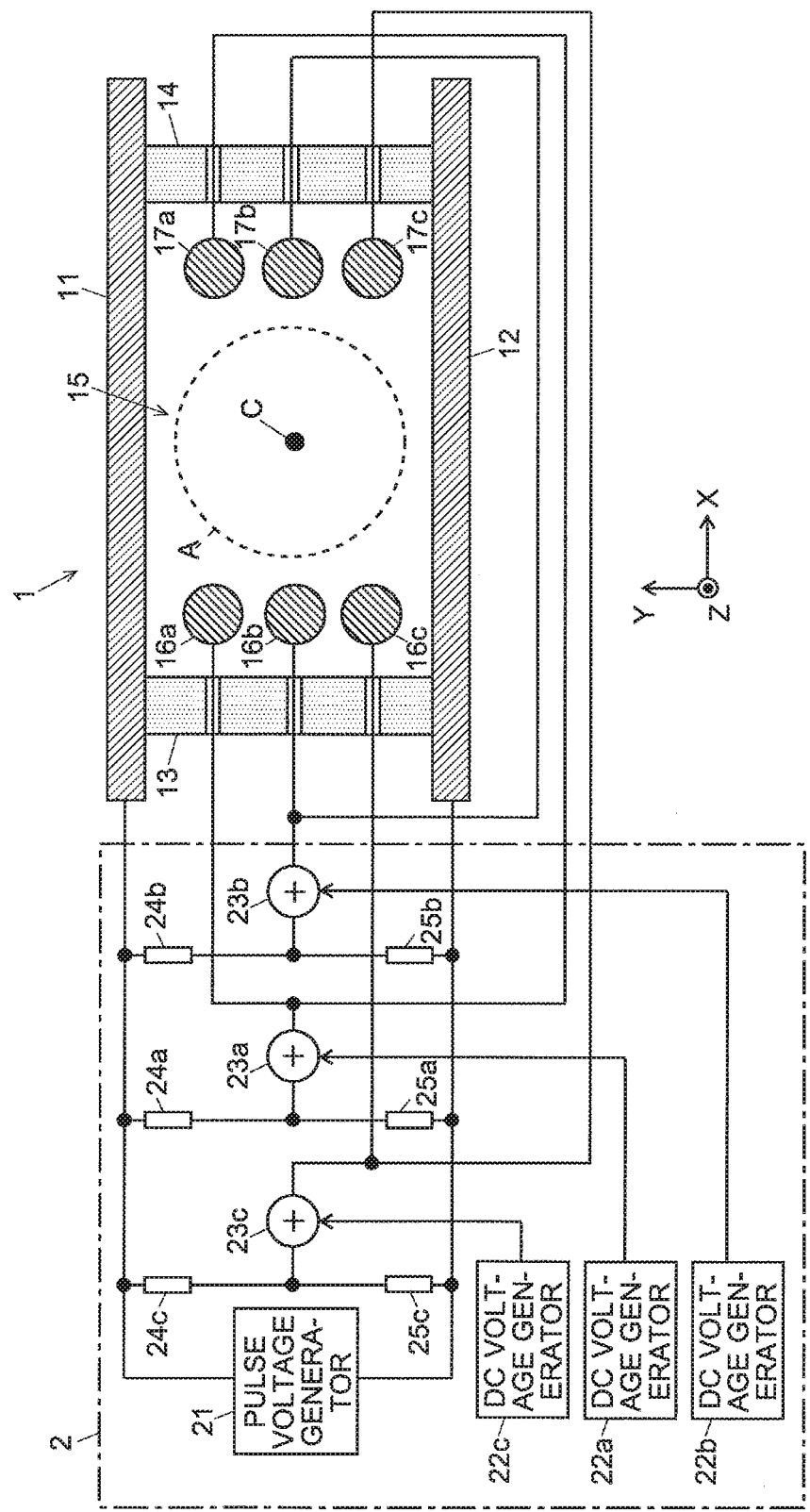
FIG. 5 is a schematic configuration diagram of an ion separator section in an ion mobility spectrometer as another embodiment of the present invention.

FIG. 5 is a schematic configuration diagram of the ion separator section in an ion mobility spectrometer in another embodiment of the present invention in which yet another structure is adopted. In this example, a plurality of pairs (in the present example, three pairs) of rod electrodes separated from each other in the Y-axis direction are placed between the pair of plate electrodes 11 and 12, i.e. the first pair of rod electrodes 16a and 17a, second pair of rod electrodes 16b and 17b, as well as third pair of rod electrodes 16c and 17c. In order to apply a different voltage to each pair of rod electrodes, the voltage generator 2 is provided with: a first electric-field correction voltage generator which includes two resistors 24a and 25a, a DC voltage generator 22a and a voltage adder 23a; a second electric-field correction voltage generator which includes two resistors 24b and 25b, a DC voltage generator 22b and a voltage adder 23b; and a third electric-field correction voltage generator which includes two resistors 24c and 25c, a DC voltage generator 22c and a voltage adder 23c.

In this configuration, the amplitude of the asymmetric pulse voltage applied to each rod electrode can be controlled as needed by appropriately adjusting the resistance ratio of the two resistors (24*a* and 25*a*, 24*b* and 25*b*, or 24*c* and 25*c*) serially connected in each of the first through third electric-field correction voltage generators. The offset of the voltage applied to each rod electrode can also be controlled by appropriately adjusting the voltage value of the DC voltage generated by the DC voltage generator 22*a*, 22*b* or 22*c*. By these operations, the electric-field distribution in the Y-axis direction within the space sandwiched between the plate electrodes 11 and 12 can be finely tuned into an optimum state to properly separate ions according to their mobility ratios.

Although the rod electrodes in any of the previous embodiments have a cylindrical shape, their cross-sectional outer edge does not always need to have a circular shape. For example, it may have an elliptical, polygonal, square, or rectangular shape.

In the previous embodiments, the same voltage is commonly applied to the two or plurality of rod electrodes. It is also possible to intentionally apply a slightly higher DC voltage to one rod electrode than the other one (or ones) so as to make the electric field asymmetric also in the X-axis direction and thereby shift the converging position of the ions in the X-axis direction.

It should also be noted that any change, modification or addition appropriately made within the spirit of the present invention in any aspect other than the previously described ones will naturally fall within the scope of claims of the present application.

REFERENCE SIGNS LIST

1 . . . Ion Separator Section
11 . . . Upper Plate Electrode
12 . . . Lower Plate Electrode
13, 14 . . . Spacer
15 . . . Ion Separation Space
16, 17 . . . Rod Electrode
18, 19 . . . Electrode Plate
2 . . . Voltage Generator
21 . . . Pulse Voltage Generator
22, 22*a*, 22*b*, 22*c* . . . DC Voltage Generator
23, 23*a*, 23*b*, 23*c* . . . Voltage Adder
24, 25, 24*a*, 24*b*, 24*c*, 25*a*, 25*b*, 25*c* . . . Resistor
C . . . Central Axis

The invention claimed is:

1. A parallel-plate non-uniform electric field ion mobility spectrometer including a pair of parallel plate electrodes and a main voltage generator for applying an asymmetric pulse voltage to the plate electrodes so as to create a non-uniform electric field within an ion separation space between the plate electrodes, for separating ions according to mobility by introducing ions derived from a sample component into the ion separation space while a flow of buffer gas is passed through the ion separation space at a constant flow velocity in a same direction as a direction in which the ions are introduced, and by controlling a movement of the ions by an effect of the non-uniform electric field while the ions are carried by the flow of buffer gas, the ion mobility spectrometer comprising:
  a) at least two electric-field correction electrodes located within the ion separation space sandwiched between the plate electrodes, the electric-field correction electrodes shaped like rods extending in a same direction as a passing direction of the ions and facing each other across an area where the ions pass through; and
  b) an electric-field correction voltage generator for applying, to the electric-field correction electrodes, a voltage obtained by adding a predetermined DC voltage and a pulse voltage synchronized with the asymmetric pulse voltage.

2. The parallel-plate non-uniform electric field ion mobility spectrometer according to claim 1, wherein the electric-field correction voltage generator adds the predetermined DC voltage and a pulse voltage generated from the asymmetric pulse voltage by resistive division.

3. The parallel-plate non-uniform electric field ion mobility spectrometer according to claim 1, wherein a cross-sectional outer-edge shape of the electric-field correction electrodes is selected from circular, elliptical, polygonal, square and rectangular shapes.

4. The parallel-plate non-uniform electric field ion mobility spectrometer according to claim 1, wherein the electric-field correction electrodes has an extended portion reaching beyond an ion exit end of the plate electrodes.

5. The parallel-plate non-uniform electric field ion mobility spectrometer according to claim 1, wherein the main voltage generator applies, to one of the pair of plate electrodes, an additional DC voltage higher than a potential of the other plate electrode, and the electric-field correction voltage generator applies, to one of a pair of the electric-field correction electrodes facing each other across an ion stream, an additional DC voltage higher than a potential of the other electric-field correction electrode.

6. The parallel-plate non-uniform electric field ion mobility spectrometer according to claim 1, comprising a single detector having a size that allows selective detection of only one ion stream having a specific mobility ratio among a plurality of ion streams formed by the ions separated by mobility ratio as a result of passing through the ion separation space, the single detector placed at a position at which the ion stream concerned arrives.

7. The parallel-plate non-uniform electric field ion mobility spectrometer according to claim 1, comprising two or more detectors having sizes that allow respective and selective detection of two or more ion streams among a plurality of ion streams formed by the ions separated by mobility ratio as a result of passing through the ion separation space, the two or more detectors placed at positions at which the two or more ion streams respectively arrive.

8. The parallel-plate non-uniform electric field ion mobility spectrometer according to claim 1, comprising a single position-sensitive detector placed at positions at which two or more ion streams having specific mobility ratios which differ from each other arrive among a plurality of ion streams formed by the ions separated by mobility ratio as a result of passing through the ion separation space, so as to separately detect each of the two or more ion streams with the position-sensitive detector.

9. The parallel-plate non-uniform electric field ion mobility spectrometer according to claim 1, comprising three or more of the electric-field correction electrodes arranged parallel to each other within a space between the pair of plate electrodes and spaced in a planer direction of the plate electrodes so that each space formed between the neighboring electric-field correction electrodes serves as the ion separation space.

10. The parallel-plate non-uniform electric field ion mobility spectrometer according to claim 1, wherein:
  two or more groups of the electric-field correction electrodes separated from each other in a direction orthogonal to the plate electrodes are provided, each group including a plurality of electrodes facing each other across an area where ions pass through; and the electric-field correction voltage generator is capable of applying a different voltage for each of the two or more groups of the electric-field correction electrodes.

* * * * *